United States Patent [19]

Brown et al.

[11] Patent Number: 5,077,667

[45] Date of Patent: Dec. 31, 1991

[54] MEASUREMENT OF THE APPROXIMATE ELAPSED TIME OF VENTRICULAR FIBRILLATION AND MONITORING THE RESPONSE OF THE HEART TO THERAPY

[75] Inventors: Charles G. Brown; Roger Dzwonczyk, both of Columbus, Ohio

[73] Assignee: The Ohio State University, Columbus, Ohio

[21] Appl. No.: 537,365

[22] Filed: Jun. 13, 1990

Related U.S. Application Data

[63] Continuation-in-part of Ser. No. 378,426, Jul. 10, 1989, abandoned.

[51] Int. Cl.$^5$ .................. G06F 15/42; A61B 5/046
[52] U.S. Cl. ........................... 364/413.05; 128/705
[58] Field of Search ................. 364/413.05, 413.06; 128/702, 705, 419 D

[56] References Cited

U.S. PATENT DOCUMENTS

| | | | |
|---|---|---|---|
| 4,296,755 | 10/1981 | Judell | 128/705 |
| 4,680,708 | 7/1987 | Ambos | 364/413.06 |
| 4,924,875 | 5/1990 | Chamoun | 128/696 |
| 4,974,162 | 11/1990 | Siegel et al. | 364/413.06 |

OTHER PUBLICATIONS

Nygards et al., "Recognition of ventricular fibrillation utilizing the power spectrum of the ECG", Conference: Computers in Cardiology, Rotterdam, Netherlands, Sep. 29 to Oct. 1, 1977, pp. 393-397 (abstract only).

Kuo et al., "Computer Detection of ventricular fibrillation", Conference: Computers in Cardiology 1978, Sep. 12-14, 1978, Stanford, CA, pp. 347-349 (abstract only).

Herbschleb et al., "Frequency analysis of the ECG before and during ventricular fibrillation", Conference: Computers in Cardiology, Williamsburg, VA, Oct. 22-24, 1980, pp. 365-368 (abstract only).

Nolle et al., "Power spectrum analysis of ventricular fibrillation and imitative artifacts", Conference: Computers in Cardiology, Williamsburg, VA, Oct. 22-24, 1980, pp. 209-212 (abstract only).

Forster et al., "Recognition of ventricular fibrillation, other rhythms and noise in patients developing the sudden cardiac death syndrome", Conference: Computers in Cardiology, Ninth Meeting of Computers in Cardiology, Seattle, WA, Oct. 12-15, 1982, pp. 245-248 (abstract only).

Martin et al., "Effects of calcium antagonists on the time course of ECG power spectrum during ventricular fibrillation", Computers in Cardiology, 1983, pp. 213-216.

Martin et al., "Differences in the time course of the power spectrum during ventricular fibrillation", The Application of Computers in Cardiology, 1984, pp. 179-183.

Martin et al., "Relation between power spectrum time course during ventricular fibrillation and electromechanical dissociation: Effects of coronary perfusion and nifedipine" European Heart Journal, No. 7, 1986, pp. 560-569.

Primary Examiner—Jerry Smith
Assistant Examiner—David Huntley
Attorney, Agent, or Firm—Frank H. Foster

[57] ABSTRACT

The approximate elapsed time since the onset of ventricular fibrillation is detected from an analog electrocardiogram signal. The signal is digitized for a time interval of four seconds to obtain a data set of time domain samples. These time domain samples are Fourier transformed to a frequency domain spectrum and the median frequency which bisects the energy of the power spectrum is detected. That median frequency is then compared to a pattern of experimentally obtained median frequency data as represented by a mathematical algorithm to calculate the estimated time from the onset of ventricular fibrillation. This frequency parameter can also be used to evaluate the response to therapy during ventricular fibrillation and CPR, as well as estimate the most appropriate time to defibrillate a subject following various pharmacologic and mechanical intervention.

9 Claims, 16 Drawing Sheets

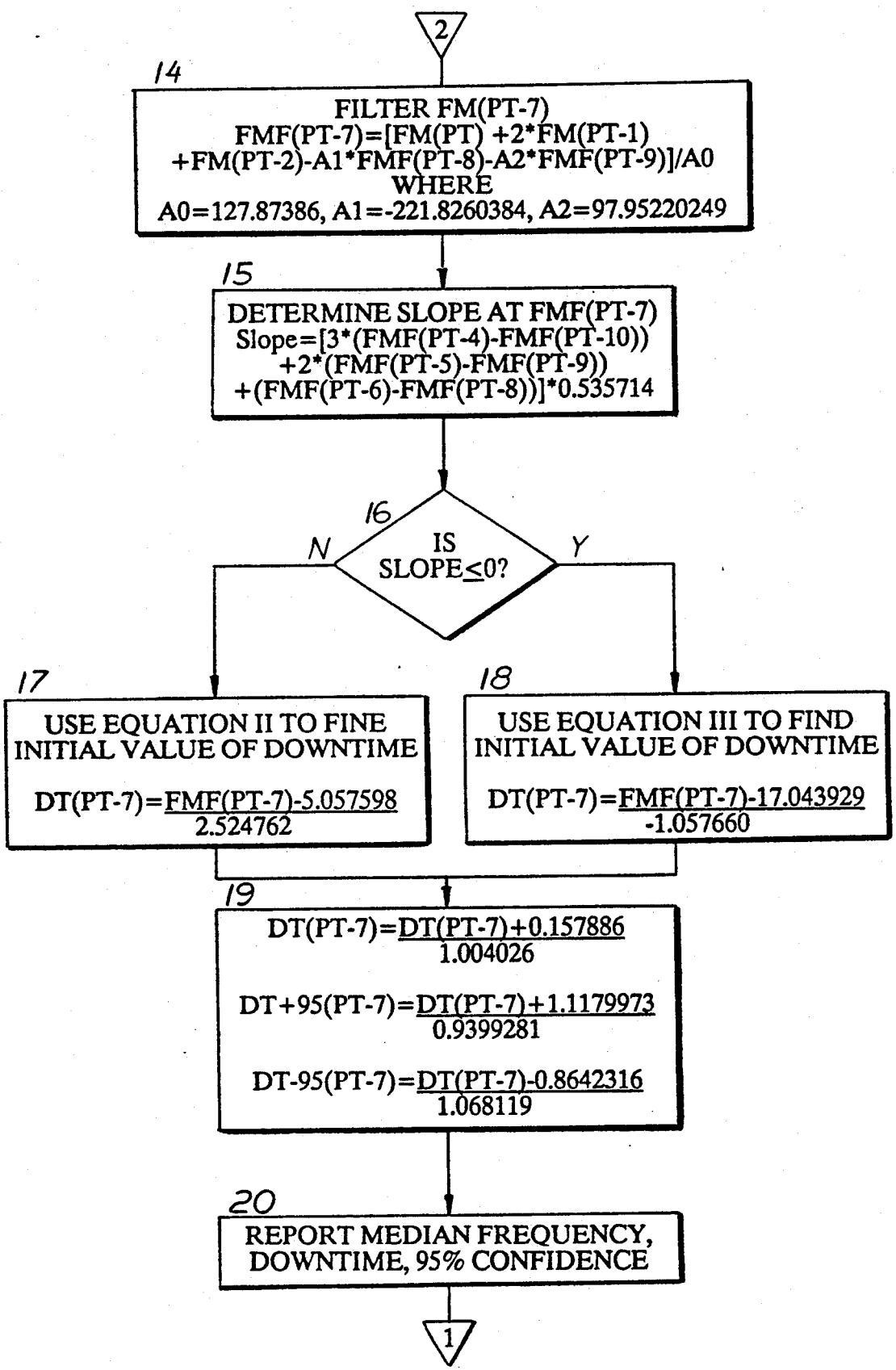

MEASUREMENT OF THE APPROXIMATE ELAPSED TIME OF VENTRICULAR FIBRILLATION AND MONITORING THE RESPONSE OF THE HEART TO THERAPY

This application is a continuation-in-part of application Ser. No. 07/378,426, filed on July 10, 1989 and now abandoned.

TECHNICAL FIELD

This invention relates generally to electronic equipment utilized in the medical field for obtaining medical information from a subject and more particularly relates to an apparatus which is connected to an electrocardiogram monitor to measure a characteristic of the fibrillating heart of a subject which is useful to a treating physician in his or her decisions in determining the course of treatment. The measured characteristic is useful for estimating the approximate elapsed time since the onset of ventricular fibrillation in a subject and for monitoring the response of the heart to therapeutic intervention to assist in selecting the most appropriate time to attempt defibrillation. This invention is applicable to ventricular fibrillation, not atrial fibrillation and therefore is applicable in the presence of both.

BACKGROUND ART

Approximately 600,000 subjects annually suffer a cardiac arrest outside the hospital. Nearly three-fourths of these subjects are found in ventricular fibrillation. The currently recommended treatment for ventricular fibrillation is the application of closed chest, cardiopulmonary resuscitation and the institution of transthoracic defibrillation. This therapy is usually carried out by pre-hospital emergency care units. While approximately one-third of the subjects found in ventricular fibrillation can be successfully defibrillated into a cardiac rhythm that allows normal perfusion to occur, unfortunately the remaining two-thirds are not. There are many factors which contribute to unsuccessful defibrillation, including underlying ischemic heart disease and prolonged ischemia times prior to therapy.

Recent studies suggest that subjects who have been in ventricular fibrillation for a more extensive time period would be better treated by alternative therapy prior to defibrillation rather than transthoracic defibrillation initially. Some studies indicate that transthoracic defibrillation may actually cause myocardial damage and hinder efforts at successful resuscitation as downtime, the elapsed time since the onset of ventricular fibrillation, increases and the myocardium's supply of high energy phosphates becomes depleted. When insufficient high energy phosphates remain to permit normal myocardial contraction to occur following defibrillation, definitive therapy should instead be directed at restoring myocardial metabolism and the regeneration of high energy phosphates prior to the application of transthoracic defibrillation.

While several recent studies have shown that the level of blood flow generated during cardiopulmonary resuscitation is insufficient to meet the metabolic demands of a fibrillating myocardium, newer therapies aimed at improving myocardial blood flow and increasing myocardial oxygen delivery over myocardial oxygen consumption, may be more appropriate than initial defibrillation therapy in subjects suffering a prolonged period of ventricular fibrillation. As the duration of ischemia progresses, the ability to successfully defibrillate the fibrillating myocardium decreases.

Clinical observations support this approach and suggest that subjects who are found early after the onset of ventricular fibrillation are most amenable to defibrillation therapy, while subjects suffering a more prolonged downtime may be more amenable to techniques which improve myocardial blood flow and myocardial oxygen supply and regenerate high energy phosphates prior to the application of defibrillation therapy. Clinical observations suggest that subjects are likely to respond well to transthoracic defibrillation if less than 4 minutes have elapsed since the onset of ventricular fibrillation and to respond poorly if more than 7 minutes have elapsed. We have found more specifically that 5 minutes is the approximate boundary between a probable successful defibrillation and a probable lack of success in the absence of therapeutic intervention.

The difficulty with applying these concepts to choose the preferred therapy is that they require a knowledge of whether the time lapse since the onset of ventricular fibrillation is sufficiently short that transthoracic defibrillation is indicated or is sufficiently long that the alternative preliminary therapy is indicated. In a typical cardiac arrest emergency situation a finite time is necessary for the arrival of emergency medical assistance. In addition, witnesses are in an excited and stressed mental state making their estimates of the downtime unreliable. No device exists which can provide an accurate estimate of the time lapse since the onset of ventricular fibrillation prior to the initiation of therapy so that the time information may be utilized to select the appropriate therapy. Thus, the problem is how to determine downtime.

Others have previously observed that the average amplitude of the ECG signal decreases subsequent to the onset of ventricular fibrillation. This time domain signal amplitude decreases exponentially until eventually the signal disappears altogether. In practice, the ECG signal, during ventricular fibrillation, is classified as being composed of either coarse (high amplitude) or fine (low amplitude) waves. This amplitude based classification provides an emergency medical team with a rough indication of the results they can expect from their defibrillation efforts. Amplitude, however, varies from subject to subject and is dependent upon not only the time elapsed since the onset of ventricular fibrillation, but also upon body characteristics, probe/skin interface impedance, and instrumentation. As a result, there is great inter-subject variation in amplitude and therefore amplitude data gathered from one subject is not applicable to other subjects.

It is therefore an object and feature of this invention to provide a non-invasive method and apparatus for detecting downtime and which can be conveniently and quickly used by emergency medical personnel who are confronted with a subject in cardiac arrest.

Another object and feature of the invention is to measure a characteristic of a fibrillating heart after some therapeutic intervention which characteristic indicates the response of the heart to that therapeutic intervention. Such therapeutic intervention might include the administration of an agent for improving the metabolic state of the heart and/or a mechanical intervention such as the use of a ventricular assist device or manual massage of the heart. Continuously monitoring this characteristic after the intervention assists the physician in determining when defibrillation should be applied.

Another object and feature of the present invention is to provide an electronic device which is conveniently and permanently attached to a standard electrocardiogram monitor of the type currently available for emergency medical use and which provides a conditioned analog ECG output signal and a power source for the device.

A further object and feature of the invention is to provide a method for obtaining an approximation of the elapsed time since the onset of ventricular fibrillation which method is wholly independent of the body characteristics of the subject, the impedance of the connection of the ECG monitor to the subject and the gain factors of the instrumentation.

BRIEF DESCRIPTION OF INVENTION

The invention is a method for measuring a clinically useful characteristic of the fibrillating heart of a subject. The term subject is used to refer to both human and non-human animals. The measured characteristic is the median frequency of the electrical activity of the fibrillating heart. The median frequency is the frequency which bisects the energy in the power spectrum derived from the cardiac electrical signal. This measured characteristic correlates with the approximate elapsed time since the onset of ventricular fibrillation of the heart and also correlates with the heart's receptiveness to successful defibrillation following the administration of therapeutic intervention.

The invention comprises connecting electrodes to the body of the subject and detecting from the electrodes an analog electrical potential which is proportional to the electrical potential generated by the fibrillating heart. These analog signals are sampled for a selected interval of time to obtain a set of time domain samples. The power distribution of the fibrillating heart is then detected by machine transforming the time domain samples to a frequency domain power spectrum by a conventional fast Fourier transform in a machine. The median frequency is then detected from the power domain spectrum. The median frequency is that frequency on both sides of which occurs equal quantities of energy in the power spectrum. Thus, that frequency is detected at which the energy of the fibrillating heart is equally distributed among frequencies above the detected median frequency and frequencies below the detected median frequency.

Experimentally derived data are first obtained by inducing ventricular fibrillation in each of a plurality of laboratory subjects and monitoring the analog electrocardiogram signal for each subject. Each analog electrocardiogram signal is digitized for each of a plurality of sequential, selected time intervals to obtain a data set of time domain samples for each time interval. Then each data set of time domain samples is transformed by Fourier transformation to a frequency domain power spectrum. For each frequency domain power spectrum, a frequency parameter is detected which represents or defines the power distribution in the power spectrum. The preferred parameter is the median frequency of the spectrum. A model algorithm is then selected which is a mathematical algorithm which approximates or models the pattern of the frequency parameters for the experimentally derived data as a function of time.

To detect the approximate elapsed time since the onset of ventricular fibrillation in a particular subject, the analog electrocardiogram signal is digitized over a selected interval of time to obtain a data set of time domain samples. The samples are then transformed by a Fourier transformation to a frequency domain power spectrum. A frequency parameter representing the power spectrum and like the parameter used for obtaining the experimental data is detected. The frequency parameter is filtered digitally to remove any inherent noise. The estimated elapsed time since the onset of ventricular fibrillation is then obtained from the model algorithm using the frequency parameter detected for the subject. Effectively this compares the frequency parameter for the subject to the experimentally derived data to determine where the subject is with respect to the experimentally determined pattern of the frequency parameter as a function of time. A confidence interval for the estimate of downtime is also determined by comparing the estimated downtime with the experimental data.

BRIEF DESCRIPTION OF DRAWINGS

FIGS. 6A, 6B, 7, and 8 are computer flow charts illustrating the method of the present invention.

Figure 1:
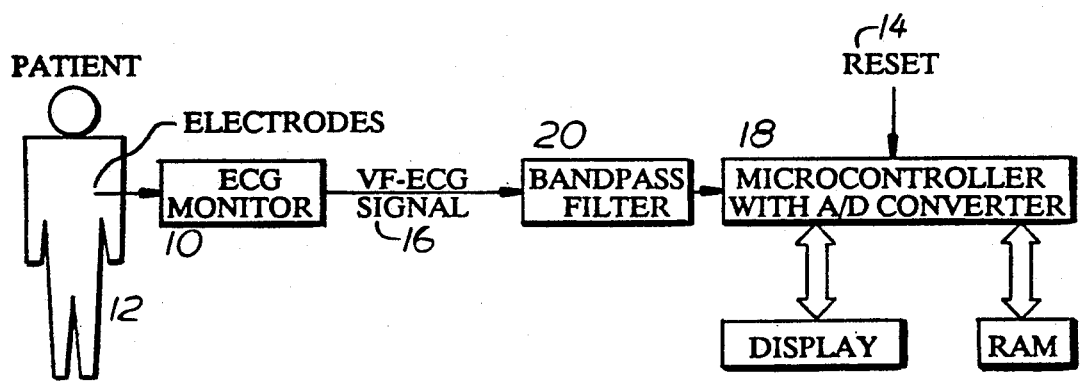
FIG. 1 and FIG. 1A are a diagrammatic block diagrams illustrating the arrangement of the apparatus

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word "connected" or terms similar thereto are often used. They are not limited to direct connection but include connection through other circuit elements where such connection is recognized as being equivalent by those skilled in the art.

DETAILED DESCRIPTION

We have found that, if the ECG signal during ventricular fibrillation is transformed by Fourier transformation from the analog time domain to a power spectrum in the frequency domain, a clear repeatable pattern occurs in the distribution of the energy in the power spectrum as a function of downtime.

Described generally, the power spectrum of the ventricular fibrillation ECG signal emitted during ventricular fibrillation was found to shift downwardly in frequency to an ebb level at approximately one and one-fifth minutes, then increase to a peak level at approximately three and one-half minutes and then decreases downwardly and asymptotically to a constant value. This identical pattern was repeated in numerous test subjects within a statistically narrow range of variation.

The elapsed time since the onset of ventricular fibrillation may, therefore, be obtained from an analog electrocardiogram signal of a subject by first digitizing the analog electrocardiogram signal for a selected interval of time in order to obtain a data set of time domain samples. These time domain samples are then transformed to a frequency domain power spectrum in accordance with well known Fourier analysis and computer implemented fast Fourier transforms. The power spectrum is then represented by a frequency parameter which defines the power distribution in the power spectrum. The frequency parameter is then filtered digitally to remove any inherent noise. That frequency parameter for the subject is then compared to the same frequency parameter for previously derived test data to determine at what stage of the experimentally derived pattern the subject being tested is located.

For purposes of obtaining experimental test data and for analyzing the electrocardiogram signal of a subject a parameter is needed which represents and is characteristic of the power spectrum for the time domain samples. We prefer that the frequency parameter be the median frequency of the power spectrum, that is, the frequency which bisects the area under the power spectrum. It should be apparent, however, that other parameters are possible, such as averaging, finding the mean frequency within a bandwidth, or finding the center of the band of frequencies within defined energy limits.

Figure 1A:
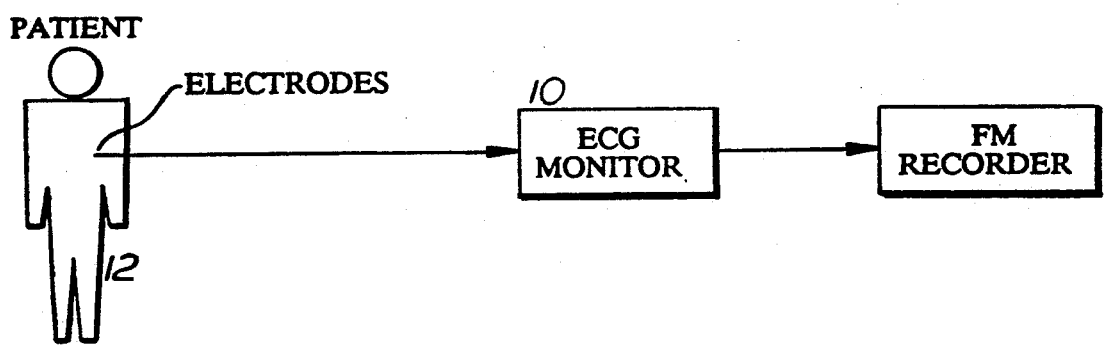

FIG. 1A illustrates an apparatus for connection to a subject in order to obtain the experimentally derived data. FIG. 1 illustrates an apparatus for connection to a subject in order to determine the time lapse since the onset of ventricular fibrillation in a particular subject. A conventional ECG monitor 10 is connected to a subject 12 in the conventional manner. Such monitors typically provide a conditioned analog ECG signal 16 as an output available on the devices. The signal is first applied to a fourth order bandpass filter 20 with a low and high cutoff frequency set at 0.5 Hz and 32 Hz respectively. From the filter the signal is applied to a port of a standard micro controller 18. The micro controller includes an on board analog to digital converter so that the analog ECG signal may be digitized. The micro controller then operates on the digital data to perform the other steps of the invention. The operation of the micro controller is started by manually resetting the device 14.

In order to obtain experimental data, eleven swine, each weighing greater than 15 kilograms, were anesthetized and a standard lead II ECG was attached. The ECG signal was continuously recorded on an FM tape recorder. The subject was then fibrillated and the ventricular fibrillation signal was recorded continuously for ten minutes. Following the experiment, the signal was digitized at 64 Hz and each four-second, 256 sample epoch was transformed into the frequency domain using a fast Fourier transform algorithm. The median frequency, FM, which is the frequency bisecting the area of the power spectrum, was determined for each power spectrum and plotted versus time for each subject.

Figure 2:
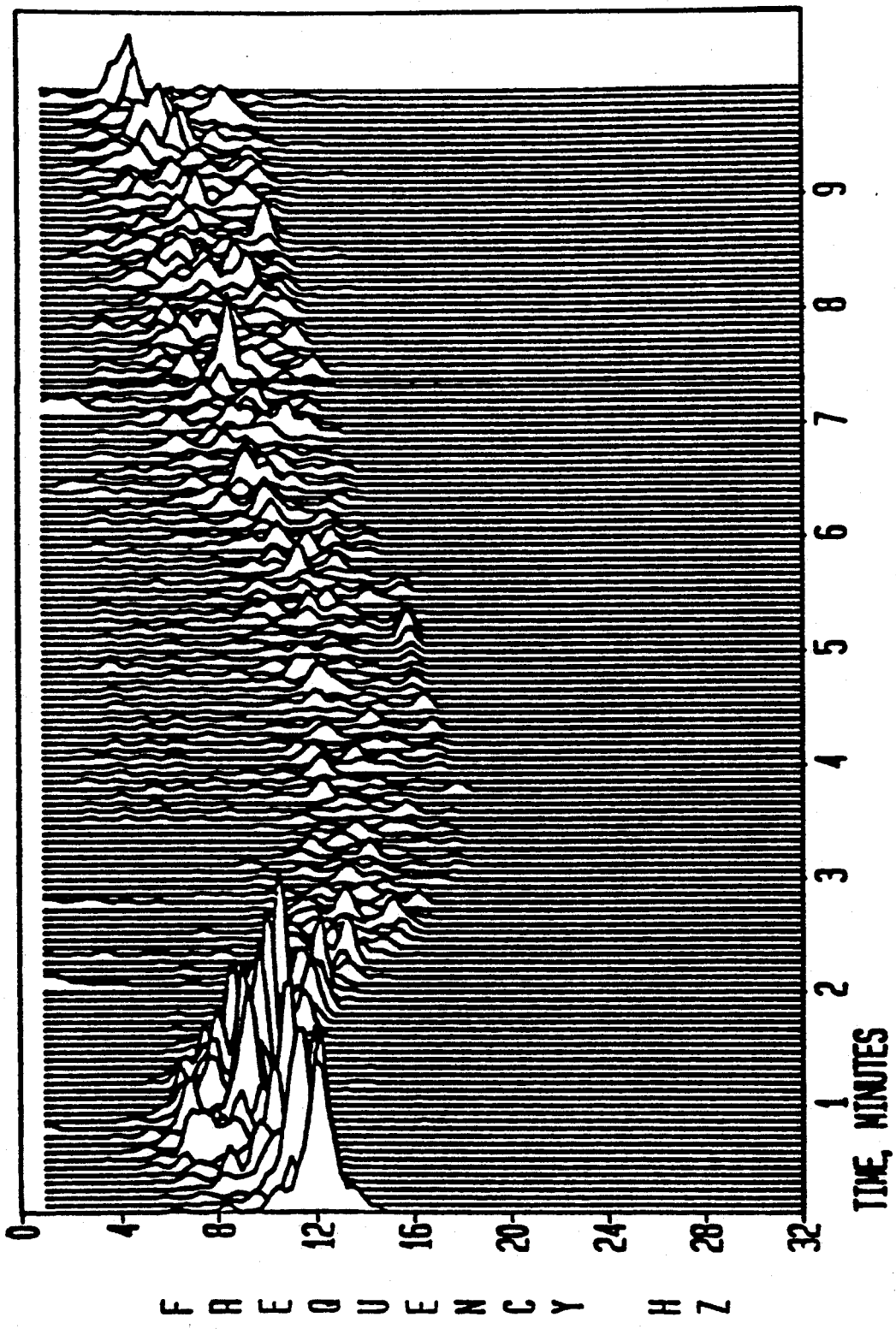
FIG. 2 is a graph illustrating compressed spectral array of the power spectrum at each of a plurality of consecutive, four second, time intervals for one subject illustrating the power spectrum pattern which is repeated in all subjects.

The ECG signal recorded from a subject in ventricular fibrillation is a sinusoidal-like signal having a maximum peak to peak amplitude of about two millivolts at the onset of ventricular fibrillation. Unlike the ECG signal from a subject with a normal sinus rhythm, the ECG, during ventricular fibrillation, has no apparent fundamental frequency but appears to be a random band-limited signal. When transformed to the frequency domain it is seen that essentially all of the energy of the signal is located in a narrow band below 20 Hz. FIG. 2 illustrates a compressed, spectral array plot of the ECG signal from one subject during ventricular fibrillation.

Figure 3:
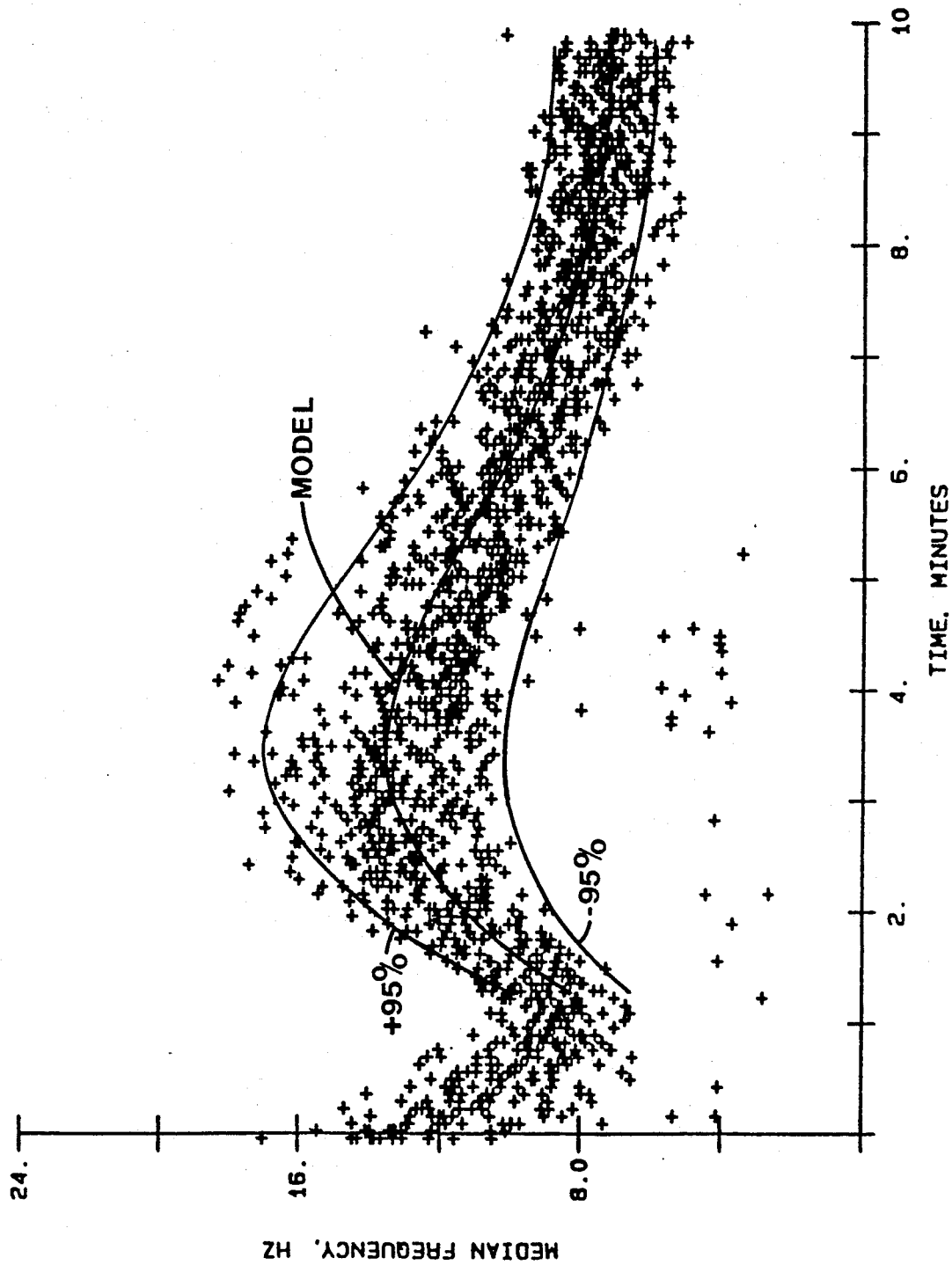
FIG. 3 is a graph illustrating the variation of a parameter defining the power distribution in the power spectra as a function of time for the eleven experimental subjects.

Referring to FIG. 3, the median frequency of each power spectrum is plotted as a function of time for all subjects. From FIGS. 2, 3, and 3A it becomes apparent that the median frequency varies from an initial value of approximately 13.5 Hz, plus or minus 1.68 Hz at the onset of ventricular fibrillation, decreases to an ebb of approximately 8.6 Hz, plus or minus 0.87 Hz, then increases to a peak of approximately 13.7 Hz, plus or minus 1.79 Hz, and then decreases steadily. Thus, there is a repeated pattern in which an ebb occurs at approximately one and one-fifth minutes, a maximum occurs at approximately three and one-half minutes, after which the median frequency decays and appears to approach a constant nonzero value asymptotically. That pattern is visible in FIG. 3A.

The pattern illustrated in FIG. 3 resembles a graph of a fourth-order polynomial, as a function of time. Therefore, at least for the period between 1 and ten minutes, the characteristic pattern of FIG. 3 may be represented by a fourth-order polynomial as follows:

$$FM(t) = a_0 + a_1 t + a_2 t^2 + a_3 t^3 + a_4 t^4 \qquad \text{Equation I}$$

where
 $FM(t)$ = median frequency of power spectrum as a function of time
 $t$ = time in minutes
 $a_0$–$a_4$ = polynomial coefficients The polynomial coefficients $a_0$–$a_4$ are experimentally determined based upon the data represented in FIG. 3. For our current experimental results the preferred coefficients are as follows:
 $a_0 = -4.08394320$ $a_1 = 13.33617585$
$a_2 = -3.38087665$
$a_3 = 0.32543629$
$a_4 = -0.01095848$ Based upon FIG. 3 and the algorithm of equation I, the median frequency FM of a particular subject can be theoretically measured by solving for t, in Equation I, given measured FM.

By definition, a fourth-order polynomial has four possible roots, i.e., values of the independent variable, for any given value of the dependent variable. In the present case, time is the independent variable and FM is the dependent variable. Two roots of Equation I lie outside the time period of interest (1–10 minutes) and can immediately be eliminated. The remaining two possible real roots of Equation I lie between 1 and 10 minutes. One lies on the rising portion of the polynomial, while the other lies on the descending portion of the curve. Therefore, to determine which root represents the proper estimate of downtime, one only needs to accumulate a number of measurements of the median frequency and then determine if the median frequency is increasing or decreasing.

The algorithm of equation I is a model algorithm which has been fitted to real data. There is variability in the data from the prediction of the model. In general, the measured FM's do not lie on the model but rather most of the data lies within the 95% confidence band that includes the model as shown in FIG. 3. It is possible, in reality, to measure an FM which is known to be within the 1–10 minute time period, but have a value which is above the highest model value within that time period Solving Equation I for that value of FM would not yield a reliable value for downtime.

Figure 4:
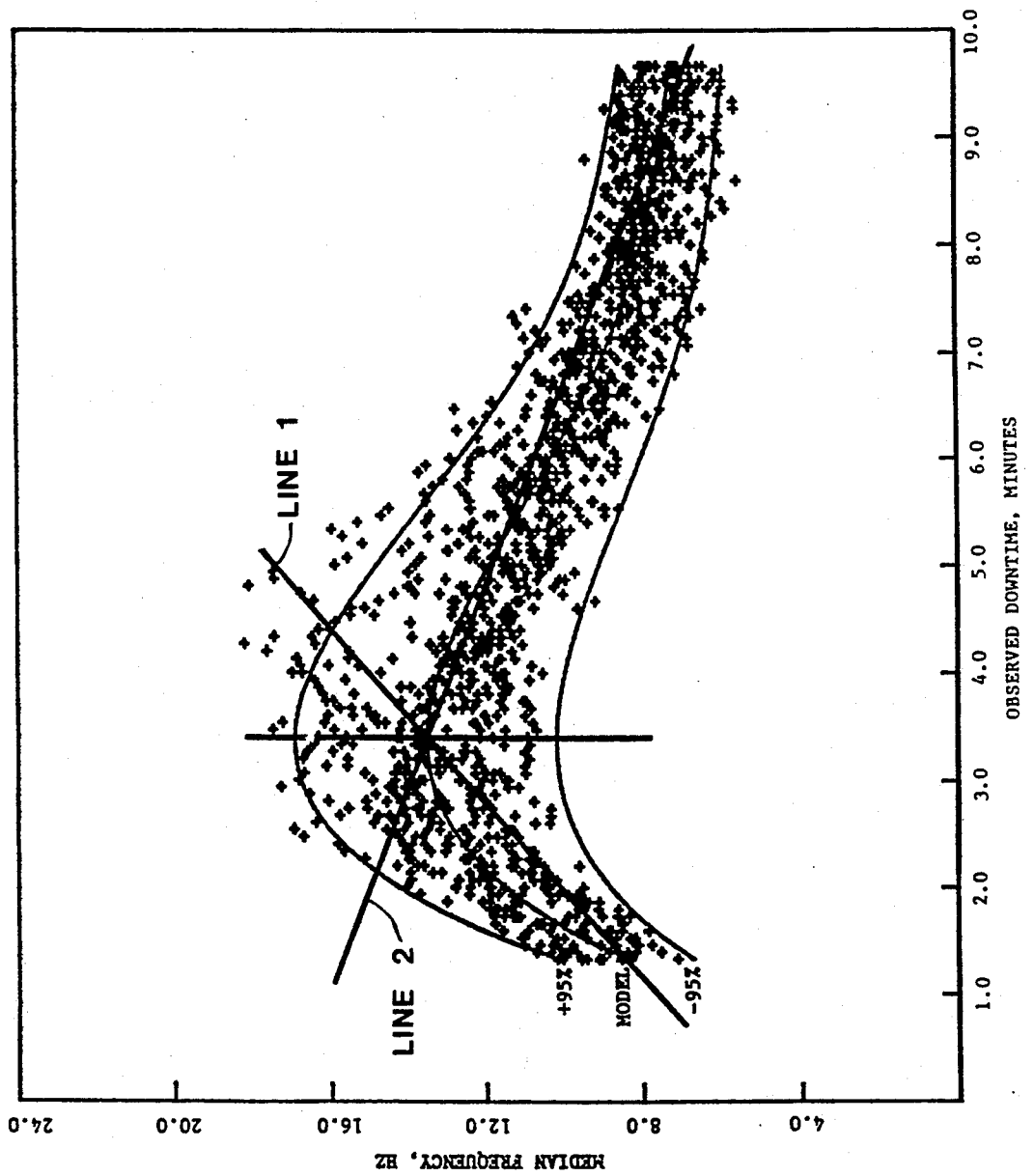
FIG. 4 is a graph illustrating the variation of a parameter defining the power distribution in the power spectra as a function of time. Also illustrated are the two first-order polynomials which approximate the fourth-order polynomial model and which are used to estimate downtime in the device.
Figure 4A:
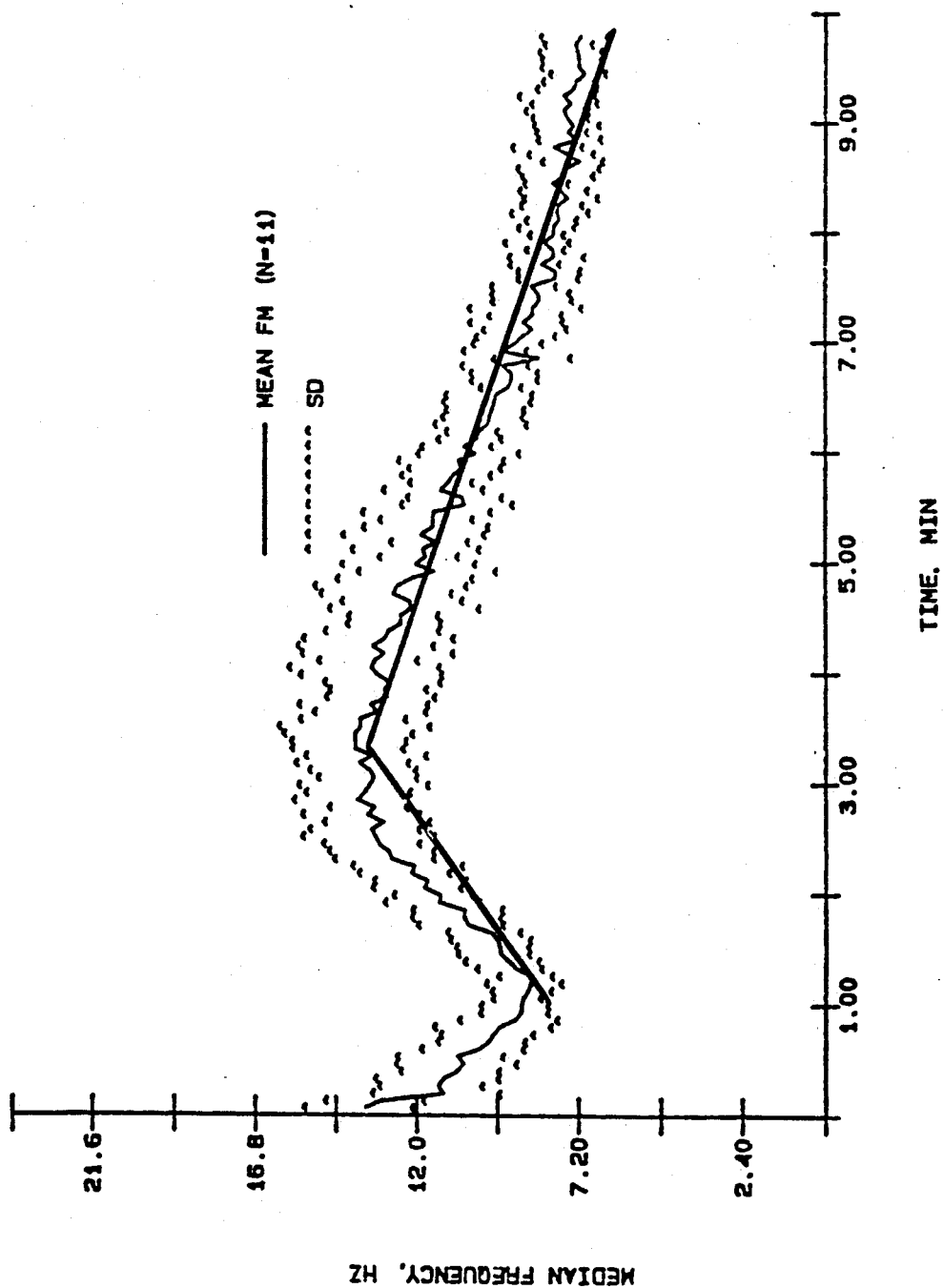
FIG. 4A shows the averaged data from FIG. 4 along with the two first order polynomials which are used to estimate downtime.

In order to overcome this problem, the fourth-order polynomial of Equation I has been approximated by two straight lines, as shown in FIGS. 4 and 4A. The first line (Line 1, FIG. 4) passes through the point at 1.34 minutes and 8.42 Hz and the point at 3.35 minutes and 13.51 Hz. This latter point represents the peak of the polynomial of Equation I. This line is represented by the equation:

$$FM(t) = 2.524762t + 5.057598 \qquad \text{Equation II}$$

The second line (Line 2, FIG. 4) passes through the point at 3.35 minutes and 13.51 HZ and the point at 9.13 minutes and 7.38 Hz. This line is represented by the equation:

$$FM(t) = -1.057669t + 17.043929 \qquad \text{Equation III}$$

Because these equations are equations of straight lines, neither of which have a slope equal to zero, a value of t exists for any measured value of FM. In order to make an initial estimate of the downtime from an observed value of FM, it is first determined whether sequential values of FM are increasing or decreasing. If FM is increasing, Equation II is used to evaluate downtime. On the other hand, if FM is decreasing, Equation III is used to evaluate downtime.

Figure 5:
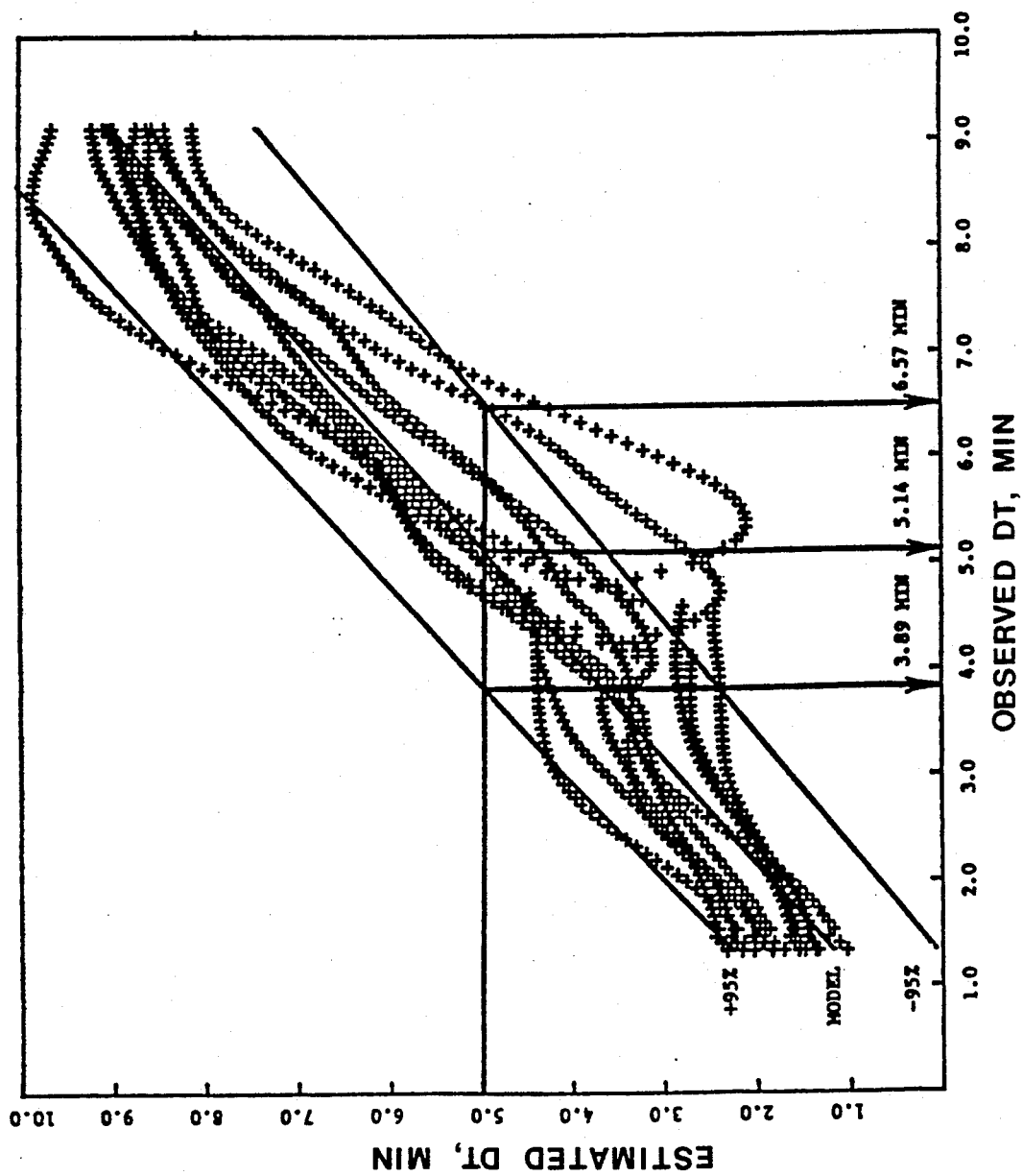
FIG. 5 is a graph illustrating estimated versus observed downtime which has been derived from the eleven experimental subjects. Also illustrated is the first-order model of this data as well as the confidence limits ($\pm 95\%$) of this model. The equation for the model and the confidence limits are used to determine an estimate of the downtime of a subject as well as the confidence limits on the estimate.

The experimental data from the eleven swine is also used to determine the final estimate of downtime as well as the confidence limits on the estimate as illustrated in FIG. 5. This graph has been constructed by plotting the downtime estimated using the technique described in the previous paragraph as a function of the observed downtime which was known a priori for all FM's measured from the experimental subjects. This data is modelled by the straight line equation:

$$t_{est} = 1.004026 t_{obs} - 0.1578860 \qquad \text{Equation IV}$$

where
$t_{est}$ = the estimated downtime, minutes, and
$t_{obs}$ = the observed downtime minutes Equations also have been derived from this data for the confidence limits for the estimate. The lower confidence limit is modelled by the equation:

$$t_{L95} = 0.9399281 t_{obs} - 1.179973 \qquad \text{Equation V}$$

where
$t_{L95}$ = lower bound on the estimated downtime, minutes

The upper confidence limit is modelled by the equation:

$$t_{U95} = 1.068119 t_{obs} + 0.8642316 \qquad \text{Equation VI}$$

where
$t_{U95}$ = upper bound on the estimated downtime, minutes

Having obtained the data, which is represented graphically in FIGS. 3, 3A, 4, 4A, and 5 and mathematically in equations I–VI, the method of the present invention may now be applied to individual subjects to obtain an estimate of the elapsed time since the onset of ventricular fibrillation. In the preferred embodiment, sequential four second time intervals of the analog ECG signal are sampled and digitized, in accordance with the present invention. We prefer to sample at a 64 Hz sample rate providing epoch of 256 samples within the four second interval. This epoch constituting a series of sequential samples is transformed into the frequency domain by conventional fast Fourier transform software. The power spectrum for each epoch is formed by squaring the magnitude of the elements of the transformed data.

The resulting squared series, which is the power spectrum, is then used to evaluate the median frequency. This is done by first summing the series to determine the total power in the power spectrum. The power series is then summed again in a sequential fashion starting from 1 Hz and continued until the sum equals one-half of the total power.

A linear interpolation algorithm is used to determine the exact frequency which bisects the area under the power spectrum. This frequency is taken as FM for that spectrum. The median frequencies are filtered digitally to remove any inherent noise.

When the device is first reset, five sequential median frequencies are determined. A second-order polynomial is fitted to these median frequencies using the least mean square error criterion. The slope of this polynomial at the center point is then evaluated. If the slope is positive, indicating that the measured FM's are increasing, then Equation II is used to estimate an initial value for downtime If, on the other hand, the slope is negative, indicating that the measured FM's are decreasing, then Equation III is used to estimate an initial value for downtime. Equations IV, V, and VI are used to calculate the final estimate of downtime and the upper and lower confidence limits of the estimate, respectively.

The invention is implemented on a computer using a fast Fourier transform, which is an efficient computer realization of the discrete Fourier transform. The discrete Fourier transform is represented by the equation:

$$H(K) = \sum_{M=0}^{N-1} H(M) * \exp(-j * 2 * pi * K * M/N) \quad \text{III.}$$

for $K = 0, 1, 2 \ldots N - 1,$ where
H(K)=discrete frequency domain signal representation,
K=discrete frequency counter,
H(M)=discrete time domain signal representation,
M=discrete time counter,
N=number of data points in the time series epoch,
frequency=K/(N*dt),
time=M*dt,
pi=3.14159 radians,
j=$\sqrt{-1}$, and
* indicates multiplication.

Figure 6A:
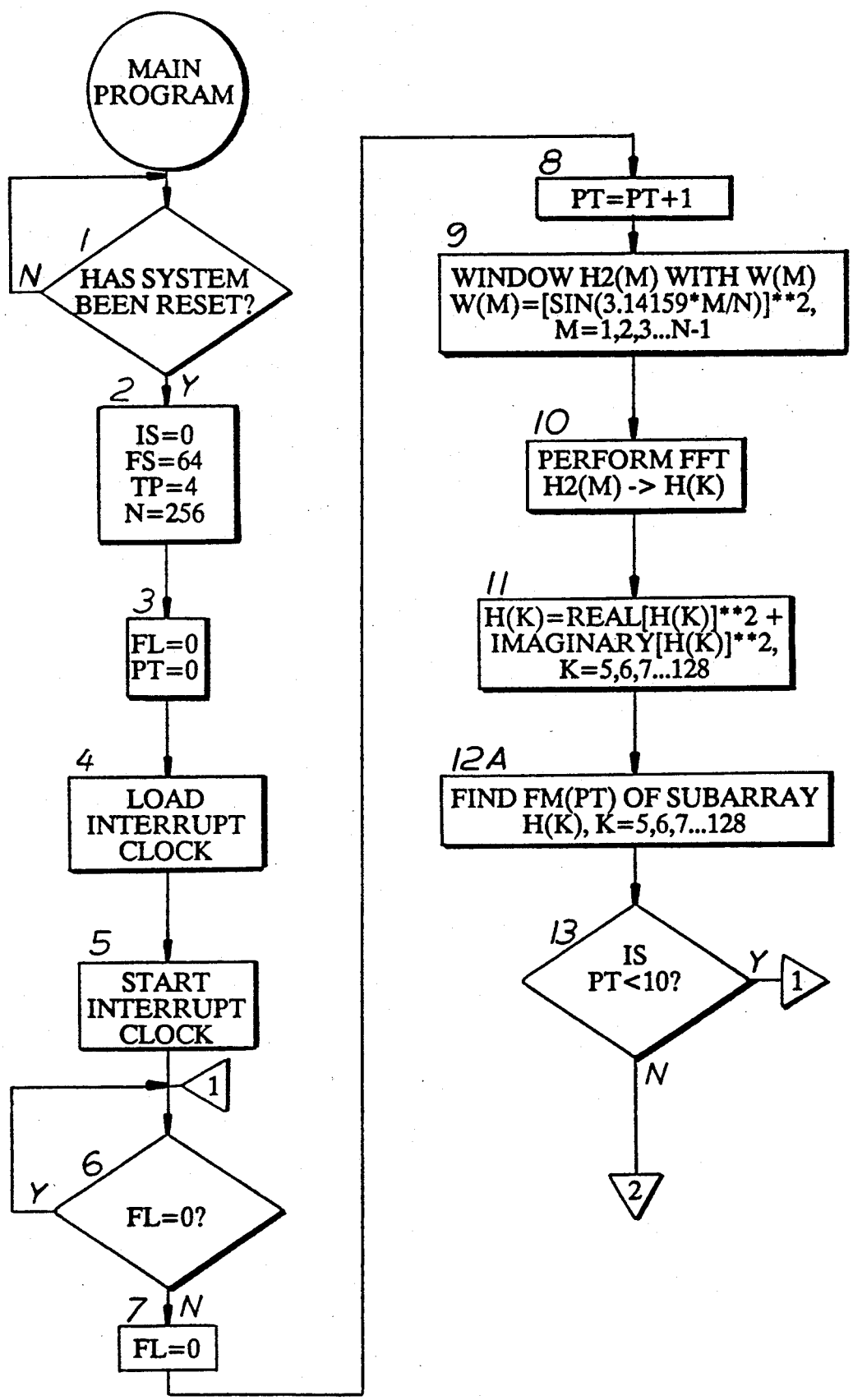
Figure 7:
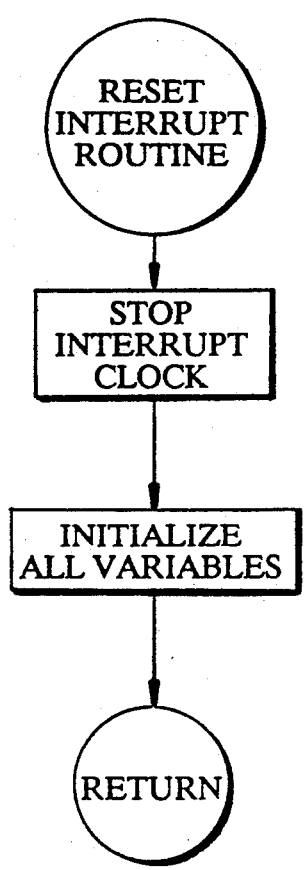
Figure 8:
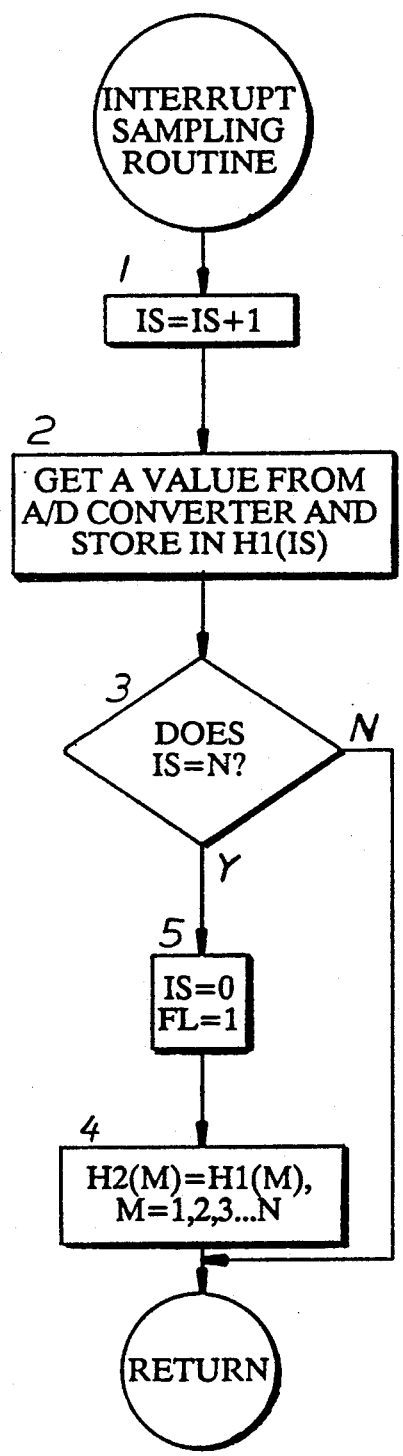

FIGS. 6, 7, and 8 illustrate in more detail the flow diagram of the main program used in the preferred embodiment of the invention.

Referring to FIG. 6, step 1 is a wait-state loop. Upon depression of the reset button of the device a signal is sent to a device embodying the present invention through connection 14 illustrated in FIG. 1. Until that happens the program loops around step 1. When the reset button is depressed the program jumps to the reset interrupt program illustrated in FIG. 7, executes it and then returns to FIG. 6.

In the reset interrupt routine, the interrupt clock which controls branching to the interrupt sampling routine is stopped so that no further branching will take place. Then all arrays are set equal to zero and control returns to step 2, FIG. 6. In step 2 the sampling parameters are initialized. IS is a counter for the H1(M) array utilized in the interrupt sampling routine and counts the number of samples taken. FS is the signal sampling rate of 64 Hz, TP is the sampling period of four seconds, and N is the epoch size of 256 samples per epoch.

In step 3 the flag FL and the pointer PT are initialized by being set to zero. FL is a flag which indicates that the sampling buffer H1(M) is full and data is ready for analysis. PT is a pointer in the several arrays where the results from the analysis are stored.

In step 4 the initialized signal sampling parameters from step 2 are loaded into the interrupt clock which is then started in step 5.

Each time the signal sampling interrupt clock times out, execution of the main program is halted and control jumps to the interrupt sampling routine. Then, when that routine is completed, the main program execution resumes. The clock will time out every 1/64 seconds to provide the 64 Hz sampling rate.

The interrupt sampling routine as shown in FIG. 8 takes a sample each time the interrupt clock times out. In step 1 the IS counter is incremented and then in step 2 a sample of the electrocardiogram signal during ventricular fibrillation is taken and stored in H1(IS). In step 3 the IS counter is compared to N to determine if all 256 samples have been taken. If IS equals N, then the buffer H1(M) is full. If IS is less than N, then control returns to the main program. If IS equals N, then the program proceeds to step 4 in which the IS counter is reset to zero and the flag FL is set to 1 to indicate that the data for a four second epoch is ready for analysis and transformation. In step 5 the data of H1(M) is loaded into the array H2(M), after which control is returned to the main program. Control will be returned to the main program at whatever step the program was about to perform when the timing out of the interrupt clock caused the program to jump to the interrupt sampling routine Returning to FIG. 6, after the interrupt clock is started at step 5, the program advances to the wait state loop of step 6. The program remains in this loop until the flag FL is set to 1, to indicate that the array H1(M) is ready for analysis and was transferred to the array H2(M) in the interrupt sampling routine.

When a full array of 256 data points are ready for analysis, control then advances to step 7 where the flag FL is reset to zero. In step 8 the pointer is incremented. In order to prevent aliasing from occurring and to force periodicity when the array is transformed into the frequency domain, the array of data H2(M) is multiplied in the conventional manner by the Hanning window function W(N) in step 9. Then in step 10 the fast Fourier transform is performed to transform the array of sample data H2(M) in the time domain to obtain the results as H(K) in the frequency domain.

The power spectrum H(K) for the band from 1 Hz to 32 Hz is obtained by summing the squares of the real and imaginary parts of H(K) for K=5, 10, 11,...129 (step The median frequency of the power spectrum H(K) is then calculated in step 12 and stored as FM(PT) as explained above. In step 13 a check is made to see if more than 9 median frequencies have been evaluated. If not, the program returns to the wait state loop of step 6 to wait until there are. If, however, more than 9 median frequencies have been evaluated, the program continues to step 14.

In step 14, the median frequency FM(PT-7) is filtered digitally to remove any inherent noise and stored in array element FMF(PT-7). The algorithm shown which performs the filtering process is an infinite impulse response digital filter which has a Butterworth type low pass response. The filter has been designed using the well known bilinear transformation method. The cutoff frequency of the filter has been chosen experimentally using the data from the eleven experimental subjects.

In step 15, the slope at FMF(PT-7) is determined. This is done by fitting a second-order polynomial to the points FMF(PT−i), i=10,9,8...4, using the least mean squared error criterion and is realized by the algorithm shown. Step 16 causes branching in the program depending on the sign of the slope. If the slope is positive program flow branches to step 17 and the initial estimate of downtime is calculated from Equation II. If the slope is negative, program flow branches to step 18 and the initial estimate of downtime is calculated from Equation III.

In step 19, the final estimate of downtime and the upper and lower confidence limits on the estimate are calculated from Equations IV, V and VI, respectively. The data is reported on the display of device and program flow jumps back to step 6 and waits for the next full buffer of data.

From the above discussion it is apparent that the median frequency, power spectrum and the resulting downtime estimate provides an indication of the physiological condition of the heart as it follows the recognizable and repeatable pattern described above following the onset of ventricular fibrillation. In the event that the time since the onset of ventricular fibrillation is sufficiently long that the attending emergency personnel decide to apply pharmacological and/or mechanical therapy instead of immediate defibrillation, the physiological deterioration of the heart may be reversed back toward normal myocardial metabolism. In that event, changes in the power spectrum and median frequency would be reversed, resulting in a measured downtime estimate that is less than the actual downtime, this reduced downtime measurement being the result of the intervention of the appropriate therapy. The sufficiently reduce downtime displayed on a device in accordance with the present invention will then indicate to the medical personnel that the appropriate time has arrived to defibrillate the subject.

Similarly, of course, the absence of a reversal of the downtime or the detection of a downtime which is sufficiently long to mandate the conclusion that irreversible myocardial and/or cerebral injury has occurred, may assist the medical personnel in concluding that further resuscitation efforts would be futile.

As explained above, we have found that the median frequency initially falls and subsequently rises to a crest and then falls downwardly as time progresses. When treatment is to be administered at times substantially after this crest, defibrillation can be more effective if therapeutic intervention is first administered, for example for improving the metabolic state of the fibrillating heart and the defibrillation is delayed until the metabolic state improves sufficiently. Studies have shown that median frequency correlates with and therefore can be used as an accurate estimate of the metabolic state of the heart during cardiopulmonary resuscitation and ventricular fibrillation. Thus, the median frequency can be continuously monitored after the therapeutic intervention. We have observed an improvement in the metabolic state of the heart following the administration of the chemical intervention. When the increase to above a selected frequency the success rate of defibrillation is improved over premature administration of defibrillation.

Therefore, monitoring the median frequency can minimize further injury to the heart caused by unsuccessful, premature attempts at defibrillation and can increase the probability of a successful defibrillation. Furthermore, a continued decline of the median frequency after one or more unsuccessful attempts to defibrillate indicates to the treating physician than the administration of some different therapeutic intervention would be appropriate.

It is possible that the selected frequency above which defibrillation should be attempted will vary among different subject species. It is desirable to choose a selected level based on experimental data. The selected level should be that level below which essentially no successful defibrillations occurred. Experiments we have conducted indicate that, for the subjects tested, the selected frequency should be approximately within the range of 7 to 8 Hz and in our data the precise selected level was found to be 7.72 Hz.

In any event, a treating physician who is aware of the correlation between the measured median frequency for the fibrillating heart, downtime and metabolic state can utilize the information available from the measured median frequency as one of the many factors which the physician must consider in determining the indicated treatment.

ADDITIONAL DESCRIPTION OF PREFERRED EMBODIMENT

There are three new technologies that will directly impact on the evaluation and management of the patient in ventricular fibrillation (and asystole). These new technologies include: (1) estimation of downtime; downtime being defined as the period of time between the onset of ventricular fibrillation and the initiation of advanced cardiac life support care (i.e., defibrillation); (2) monitoring myocardial perfusion (metabolic state of the heart) during cardiopulmonary resuscitation; and (3) determining the most appropriate time to defibrillate subject following therapeutic interventions during cardiopulmonary resuscitation and ventricular fibrillation (asystole).

It is important to present some background information in order to understand these technologies. The population of subjects include those in cardiac arrest with the underlying cardiac rhythm of ventricular fibrillation and asystole. In clinical practice this encompasses approximately 75-85% of the population of subjects having cardiac arrest. In this regard, signal (waveforms) varying in size and shape with no discernable P-wave, QRS complex, ST segment or T-wave. Asystole is defined as the absence of ventricular electrical waveforms or if ventricular activity is present, the waveforms are less than 1 mm in height. (Note: This is confirmed in two leads. P waves may be present.) To prehospital medical personnel and physicians, asystole is often interpreted from the electrocardiogram (ECG) as a "flatline" electrical signal, when, in fact, very fine ventricular fibrillation (small amplitude) may actually be present.

Figure 9:
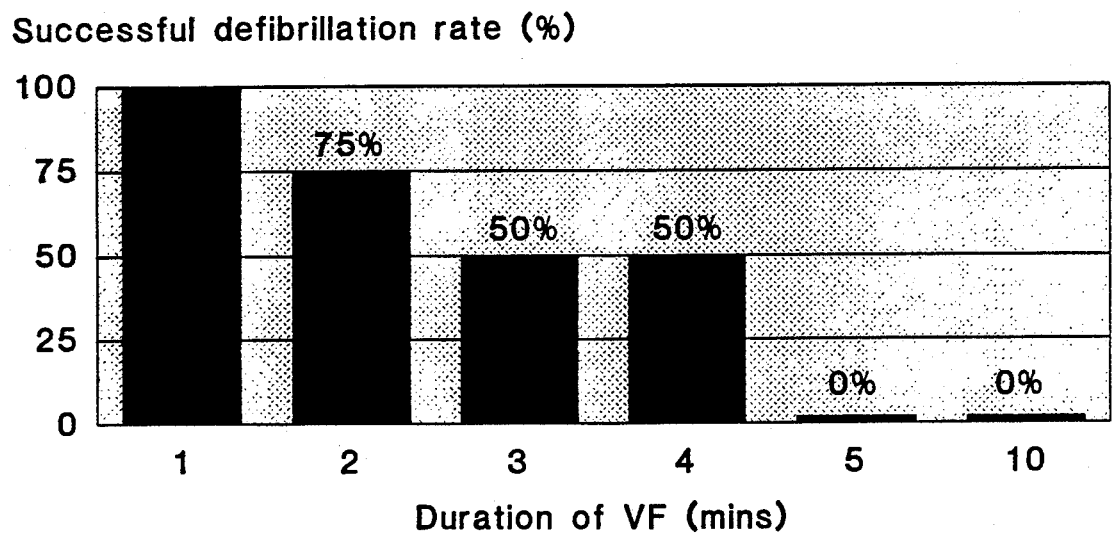
FIG. 9 refers to a compilation of experiments which looked at the relationship between the duration of ventricular fibrillation and the ability to successfully defibrillate a subject into a perfusing rhythm.

The first technology is estimation of downtime during cardiac arrest and ventricular fibrillation (asystole). The treatment of ventricular fibrillation (asystole) is dependent on downtime. FIG. 9 refers to a compilation of experiments which looked at the relationship between the duration of ventricular fibrillation and the ability to successfully defibrillate the subject into a perfusing rhythm. After varying durations of ventricular fibrillation, each subject received up to three defibrillations (with the appropriate energies based on current American Heart Association recommendations). After one minute of ventricular fibrillation, 100% of the subjects were successfully defibrillated into a perfusing rhythm. After two minutes of ventricular fibrillation, 75% of the subjects were defibrillated into a perfusing rhythm. After either three or four minutes of ventricular fibrillation, 50% of the subjects were successfully defibrillated into a perfusing rhythm. It is also clear from this figure that at five minutes of ventricular fibrillation, initial defibrillation therapy of the subject in ventricular fibrillation cardiac arrest was no longer successful. That is, after five minutes of ventricular fibrillation, initially treating a subject with up to three defibrillations is not successful in returning the heart to a spontaneously perfusing rhythm. It can also be seen from FIG. 9, that initial defibrillation therapy is ineffective beyond five minutes of ventricular fibrillation as well. Therefore, it is becoming increasingly clear that after a downtime of five minutes (or greater) therapy with defibrillation (as currently recommended by the American Heart Association Advanced Cardiac Life Support Guidelines) is not effective as the initial therapeutic intervention in the treatment of ventricular fibrillation.

In addition, there is increasing evidence to suggest that the heart may be injured by the cumulative energies imparted to it during repeated defibrillation attempts. Therefore, it makes good clinical sense to limit the number of defibrillations and the amount of energy imparted to the fibrillating myocardium to a minimum level which is sufficient to bring the heart back to a spontaneously perfusing rhythm.

Figure 10:
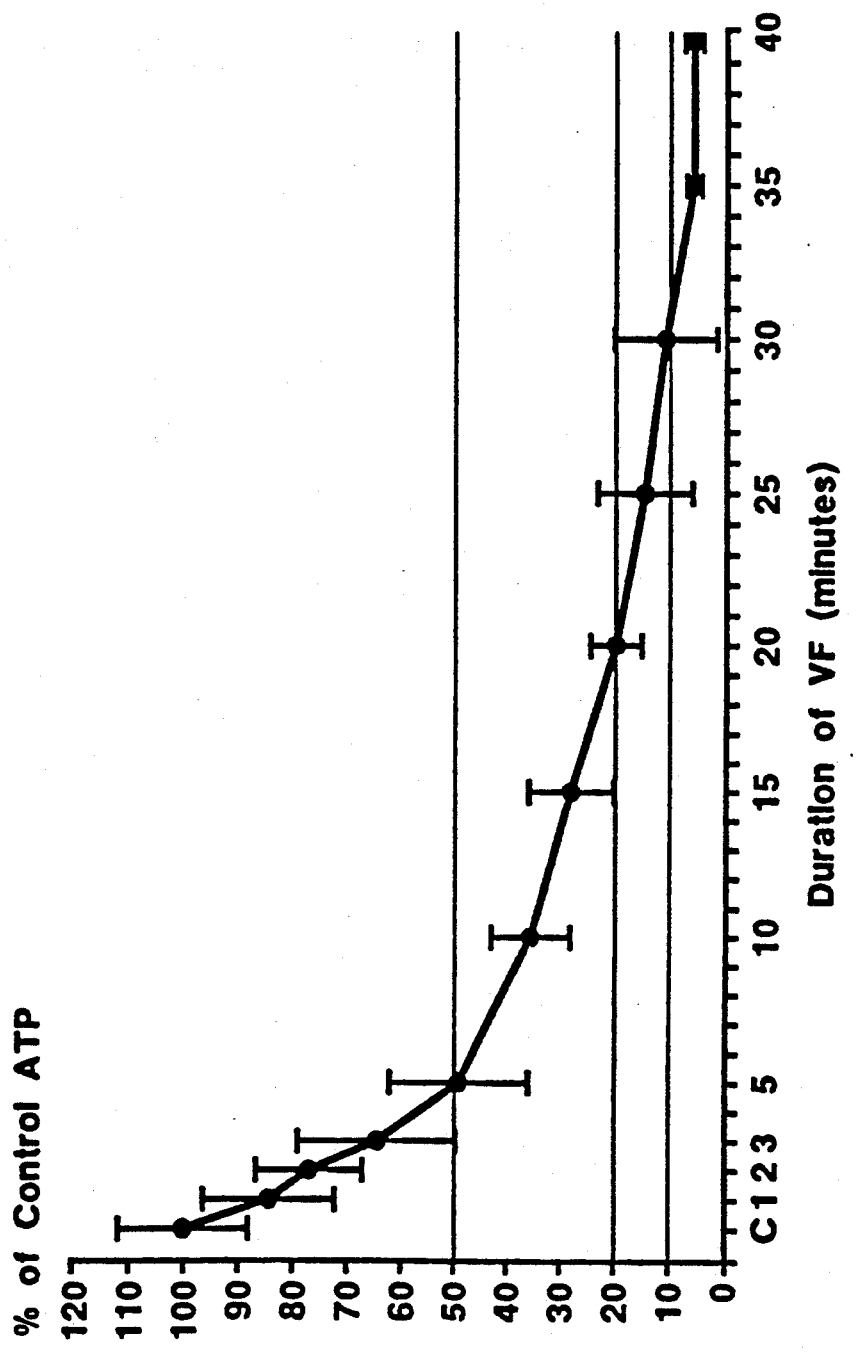
FIG. 10 is a graph of adenosine triphosphate (ATP) depletion in subjects during ventricular fibrillation.

There is also a feasible pathophysiological reason why defibrillation after five minutes of ventricular fibrillation is not effective as the initial therapeutic modality. In related studies, we determined the time frame of high-energy phosphate (adenosine triphosphate, ATP) metabolism during ventricular fibrillation. These were correlated with well established metabolic markers of myocardial injury. It is known that following ischemia, if ATP levels decline to below 50% of baseline levels, effective restoration of myocardial function is not immediately possible (stunned myocardium). The heart may need to be adequately reperfused and treated with pharmacological agents over an extended period of time prior to returning the heart to a normal contracting state. Referring to FIG. 10, 50% of the ATP was depleted at five minutes of ventricular fibrillation. From a metabolic standpoint, it appears that after five minutes of ventricular fibrillation, insufficient high-energy phosphates remain for the heart to contract normally following defibrillation. From the clinical perspective, if we were able to estimate downtime one could logically decide on the best therapeutic intervention for the subject in ventricular fibrillation. If the subject was in ventricular fibrillation for less than five minutes, initial therapy with defibrillation would be the most effective. At five minutes or greater of ventricular fibrillation, certain therapeutic interventions would have to be instituted in order to return the heart to a more favorable metabolic state (theoretically increase the high-energy phosphate ATP content) prior to defibrillation. Such therapeutic interventions may include the use of high-dose adrenergic drug therapy, mechanical interventions such as direct mechanical ventricular assistance or open-chest manual cardiac massage. After 10 to 15 minutes of ventricular fibrillation, these latter interventions, if employed as the initial therapeutic interventions can effectively improve myocardial oxygen delivery and return of spontaneous circulation following defibrillation in greater than 65% of the experimental subjects.

In addition: (1) there is increasing evidence which supports the fact that the amount of energy used to defibrillate the heart within the first five minutes of ventricular fibrillation may also be dependent on downtime; and (2) the dose of adrenergic drug used to achieve certain levels of myocardial blood flow after five minutes of ventricular fibrillation may also be dependent on downtime Therefore there is increasing evidence to suggest that the initial therapeutic intervention in the treatment of ventricular fibrillation may be dependent on downtime. Accordingly, a rapid and reliable estimation of downtime in ventricular fibrillation (asystole) is needed. While several individuals have suggested that estimations of downtime can be made from witnesses at the scene of a cardiac arrest, this is not feasible for two reasons: (1) a large percentage of cardiac arrests are not witnessed by bystanders; and (2) when witnesses are available, studies have shown that when estimates are taken from two witnesses at the scene of the same cardiac arrest, estimates of their downtime show a large degree of variability. Biochemical assays have also been suggested as a means for determining downtime, but these would be too tedious to perform and require too much time to give the health care provider any meaningful information on which to base the immediate therapy of a patient in ventricular fibrillation. Finally, it has also been suggested that the amplitude of the ventricular fibrillation signal could be used to estimate downtime. This is a very unreliable technique. (see below)

Figure 3A:
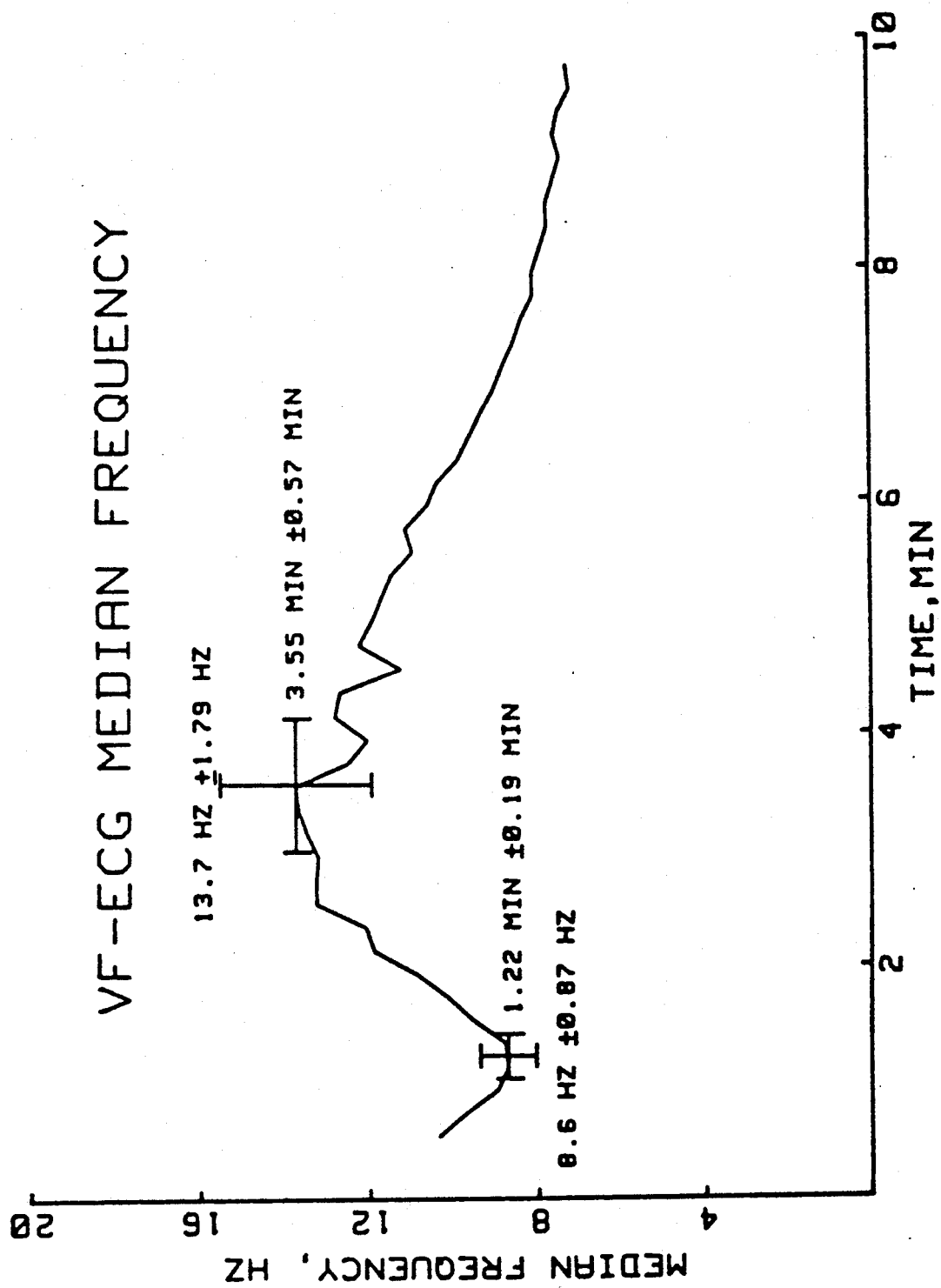
FIG. 3A is a graph illustrating the averaged variation of the median frequency for eleven experimental subjects.
Figure 11:
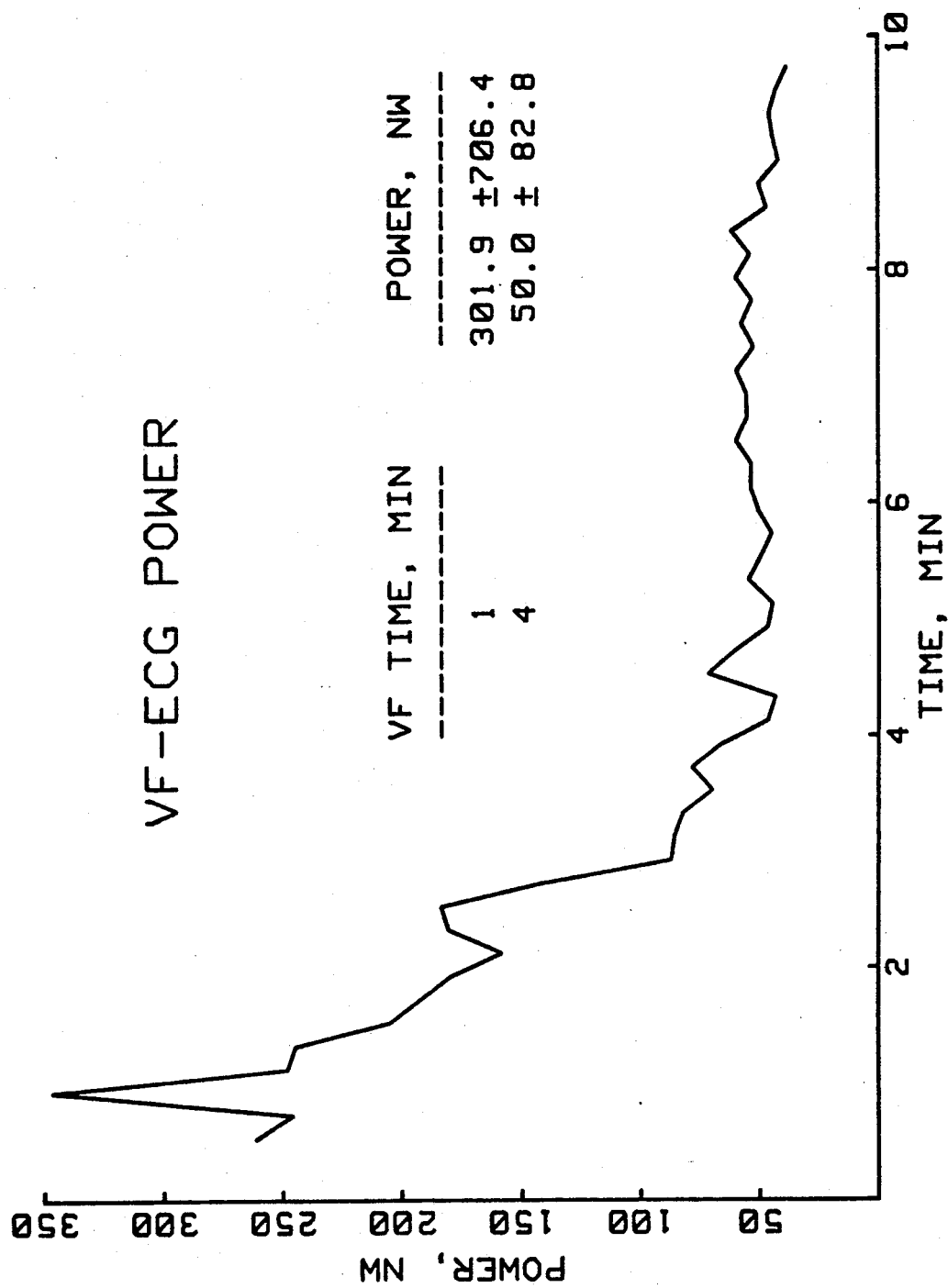
FIG. 11 is a graph of power averaged for eleven subjects in ventricular fibrillation.
Figure 12:
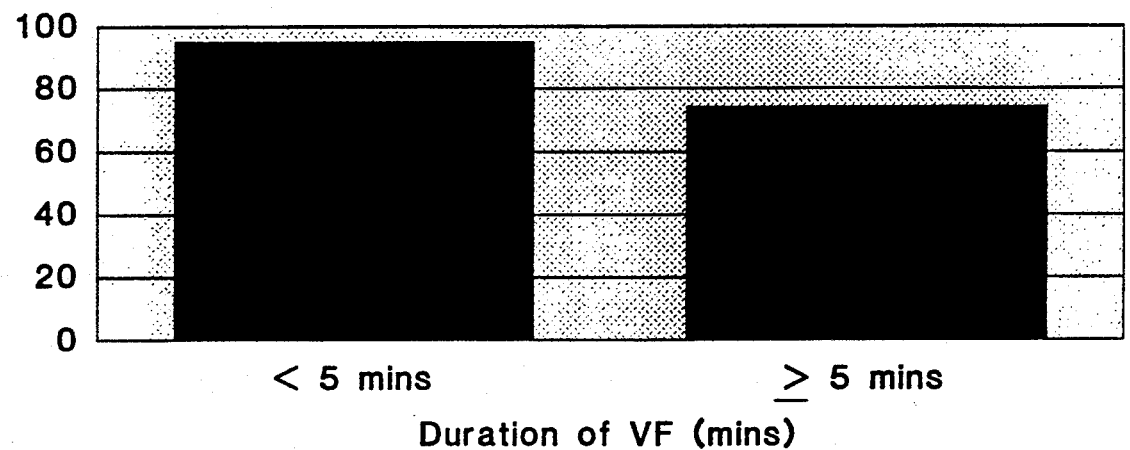
FIG. 12 is a graph of percent successful estimation of the duration of ventricular fibrillation in experimental subjects.

One of the first experiments we performed was to try to determine whether downtime could be estimated from analysis of the ventricular fibrillation signal during cardiac arrest. We placed eleven subjects in ventricular fibrillation and recorded the analog ECG signal on an FM tape recorder. The signal was digitized and the digitized signal was analyzed using a fast Fourier transform analysis. Following fast Fourier analysis, a power histogram and power spectrum are generated for each four seconds of data. From the power spectrum, several parameters were determined including: median frequency (the frequency which bisects the area under the power spectrum), bandwidth, center frequency, normalized bandwidth and power (which is the square of the amplitude of the ECG signal). Each parameter (representing four seconds of ventricular fibrillation was determined and the average (for each parameter) for all eleven subjects was plotted. The graph of the power (averaged for all 11 subjects) is seen in FIG. 11, and the graph of median frequency (averaged for all 11 subjects) is seen in FIG. 3A. Referring to FIG. 11, there is a large amount of intersubject variability in the power (or amplitude) in the ventricular fibrillation ECG signal. Therefore, power would be an unreliable parameter for estimating downtime. On the other hand, looking at the median frequency time course during ventricular fibrillation (see FIG. 3A), we see that the median frequency reaches an ebb at 1.22 minutes with a small degree of variability ($\pm 0.19$ minutes), at this time the median frequency is 8.6 Hz$\pm$0.87 Hz. This then reaches a crest at 3.55 minutes ($\pm 0.57$ minutes) at a median frequency of 13.7 Hz$\pm$1.79 Hz From there the median frequency decreases over time. These data can be modelled (see FIG. 4A) and thus by simply knowing the median frequency, and whether the median frequency is increasing or decreasing, one can accurately estimate the downtime. In fact, we looked at our ability to successfully predict downtimes of less than five minutes or greater than (or equal to) five minutes (see FIG. 2). With this model we were able to accurately predict downtimes of less than five minutes in 95% of the estimations and greater than or equal to five minutes in 77% of the estimations. Thus, from this analysis, you can see that the potential exists, by using a frequency parameter (and in this case the median frequency), to successfully estimate the downtime in these experimental subjects.

Similarly, we have now begun to obtain data from patients in ventricular fibrillation. We have only analyzed the data from seven subjects to date and thus have not modelled the data. It is of interest to note that the pattern of frequency parameter(s) previously described are qualitatively similar in humans as in prior experimental subjects. As we accumulate more data and look at these frequency parameters, it is clear that we can identify a parameter(s) that is either monotonic or has a small degree of variability and thus could be used to estimate downtime in humans.

Figure 13:
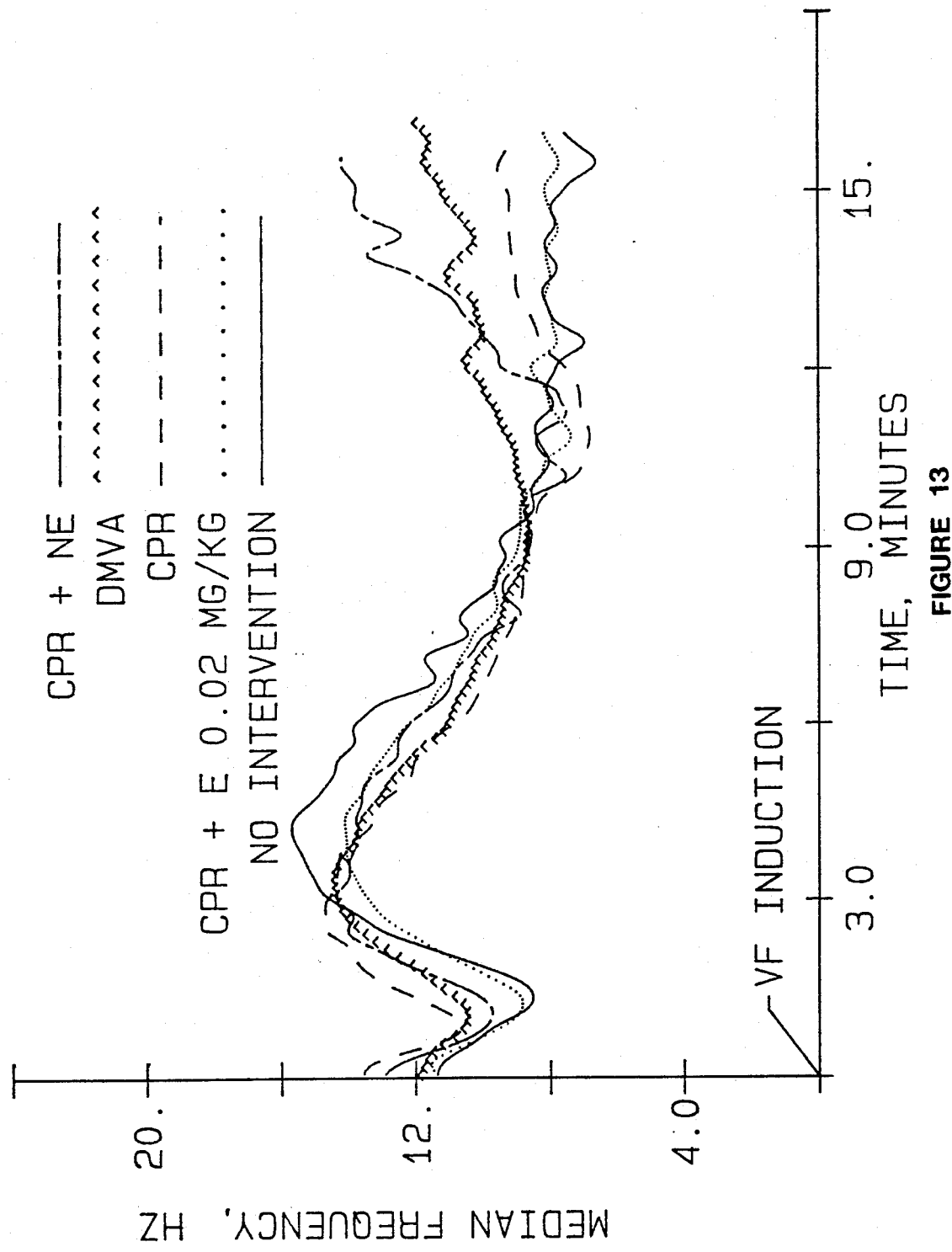
FIG. 13 is a graph of median frequency versus time for various therapeutic interventions during ventricular fibrillation in experimental subjects.

The second technology involves non-invasive monitoring of myocardial perfusion during cardiac arrest and resuscitation. After five minutes of ventricular fibrillation it is important to improve myocardial perfusion and restore the heart to a metabolic state that is more conducive to defibrillation. At that point in time (at or after five minutes of ventricular fibrillation), pre-hospital emergency medical personnel or the treating clinician would then employ a therapeutic intervention to improve the metabolic state of the heart. These interventions may include pharmacological agents, mechanical therapy, including direct mechanical ventricular assistance, or manual internal cardiac massage. Referring to FIG. 13, one of five therapeutic interventions were employed following ten minutes of cardiac arrest: (1) norepinephrine(NE); (2) epinephrine (E); (3) direct mechanical ventricular assistance (DMVA); (4) cardiopulmonary resuscitation (CPR) alone; or (5) no intervention at all. The only two interventions that successfully improved myocardial blood flow and improved myocardial oxygen delivery over myocardial consumption in this study were norepinephrine and direct mechanical ventricular assistance, and with these interventions a concomitant increase in median frequency was also seen following the institution of these interventions. The other three interventions did not improve myocardial blood flow or oxygen delivery to the heart. The median frequency either remained the same or decreased slightly in these groups. Thus, following ventricular fibrillation, the median frequency can be used as a guide to gauge the effectiveness of a therapeutic intervention at improving myocardial blood flow and myocardial oxygen delivery during cardiopulmonary resuscitation. Therefore, following pharmacologic or mechanical therapy during cardiopulmonary resuscitation an increasing median frequency correlates with improved myocardial perfusion.

Figure 14:
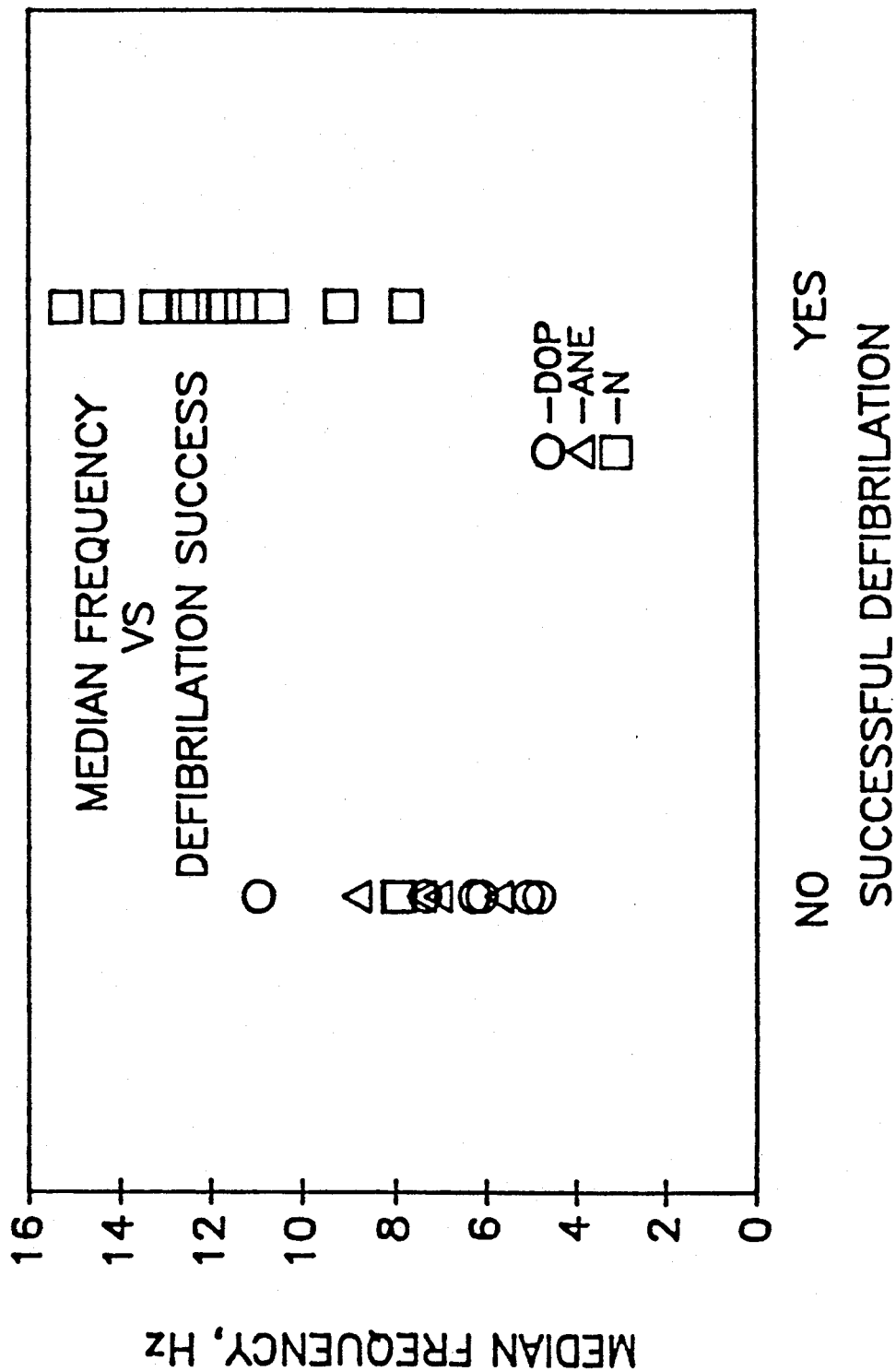
FIG. 14 is a graph of the success of defibrillation following various therapeutic interventions versus median frequency in experimental subjects during ventricular fibrillation.

Related to this technology, is a third technology. This involves predicting when to defibrillate a subject after five minutes of ventricular fibrillation. If the downtime is equal to or greater than five minutes, it appears that the most logical therapeutic intervention at that point in time would not be defibrillation, but would be to institute a pharmacological or mechanical means of reperfusing the heart sufficiently to improve oxygen delivery and thus make the fibrillating ventricle more conducive to defibrillation. Thus when the decision is made after five minutes to use a therapeutic intervention other than defibrillation, the median frequency can be used as a guide to therapy with an increasing median frequency (as previously described), correlating with improved myocardial oxygen delivery and myocardial blood flow. After ten minutes of ventricular fibrillation, one can see from FIG. 3A that median frequency runs in the range of approximately 7.0 to 7.5 Hz. From our defibrillation studies (FIG. 14), it is clear that following therapeutic interventions at this time, that if the median frequency can be increased to above 9.14 Hz, that approximately 90% of the subjects can be successfully defibrillated into a spontaneously perfusing rhythm. Parenthetically, this median frequency (9.14 Hz) correlates to the time at which initial defibrillation therapy is still successful. In addition, using median frequency as a parameter to guide defibrillation therapy after pharmacologic or mechanical interventions would also help limit the injury imparted to the myocardium following repeated defibrillation attempts.

We have developed three new technologies that can aid the health care provider in treating a patient in ventricular fibrillation and asystole. (1) This involves the initial assessment of the patient to determine downtime and thus guide initial therapy during ventricular fibrillation. If the downtime is less than five minutes, initial defibrillation therapy should be instituted. If downtime is greater than or equal to five minutes, other therapeutic modalities need to be instituted to improve the metabolic state of the heart by improving myocardial blood flow and oxygen delivery (and probably restoring high-energy phosphates). Such therapeutic interventions may include high-dose adrenergic therapy, direct mechanical ventricular assistance or internal manual open-chest cardiac massage. (2) The response to these and other interventions can then be assessed by monitoring the median frequency If the median frequency is increasing, this tells the health care provider that the metabolic state of the heart is improving. In addition, as eluded to earlier, the duration of ischemia may also dictate the best pharmacological or therapeutic modality to institute after five minutes of ventricular fibrillation, as well as the dose of pharmacological agent used. (3) As the median frequency increases after the appropriate intervention, our technology would also determine the most appropriate time to defibrillate the subject following this therapeutic intervention.

While certain preferred embodiments of the present invention have been disclosed in detail, it is to be understood that various modifications may be adopted without departing from the spirit of the invention or scope of the following claims.

We claim:
1. A method for measuring a clinically useful characteristic of the fibrillating heart of a subject which correlates with the approximate elapsed time since the onset of ventricular fibrillation of the heart, and with the metabolic state of the heart after therapeutic intervention, and for treating the subject for heart fibrillation, the method comprising:
 (a) connecting electrodes to the body of the subject and detecting from the electrodes an analog electrical potential which is proportional to the electrical potential generated by the fibrillating heart;
 (b) sampling said analog potential for a selected interval of time to obtain a set of time domain samples;
 (c) detecting the power distribution of the fibrillating heart by machine transforming said time domain samples to a frequency domain power spectrum;
 (d) detecting the median frequency which bisects the energy of said power spectrum;
 (e) treating the fibrillating heart by a therapeutic intervention;
 (f) thereafter periodically detecting said median frequency; and
 (g) treating the fibrillating heart by applying a means for defibrillation when said detected median frequency rises above a selected frequency.
2. The method of claim 1 wherein said selected frequency is approximately within the range of 7 Hz to 8 Hz.
3. The method of claim 2 wherein the selected frequency is approximately 7.7 Hz.
4. A method for measuring a clinically useful characteristic of the fibrillating heart of a subject which correlates with the approximate elapsed time since the onset of ventricular fibrillation of the heart, and with the metabolic state of the heart therapeutic intervention, the method comprising:
(a) connecting electrodes to the body of the subject and detecting from the electrodes an analog electrical potential which is proportional to the electrical potential generated by the fibrillating heart;
(b) sampling said analog potential for a selected interval of time to obtain a set of time domain samples;
(c) detecting the power distribution of the fibrillating heart by machine transforming said time domain samples to a frequency domain power spectrum;
(d) detecting the median frequency which bisects the energy of said power spectrum; and
(e) measuring the approximate elapsed time since the onset of ventricular fibrillation by comparing said measured median frequency to a model median frequency of a composite model of median frequency as a function of time, said model having been statistically derived from a plurality of prior measurements of median frequency and time elapsed since the onset of fibrillation for a plurality of similar subjects and for an elapsed time exceeding three minutes.

5. A method in accordance with claim 4 wherein said composite model is a mathematical model algorithm statistically derived from said measurements of said similar subjects.

6. A method in accordance with claim 5 wherein said model algorithm is at least two polynomials of at least first order.

7. A method in accordance with claim 6 wherein said model algorithm comprises a sequence of linear approximations of said prior measurements of similar subjects.

8. A method for measuring a clinically useful characteristic of the fibrillating heart of a subject which correlates with the approximate elapsed time since the onset of ventricular fibrillation of the heart, and with the metabolic state of the heart after therapeutic intervention, the method comprising:
(a) connecting electrodes to the body of the subject and detecting from the electrodes an analog electrical potential which s proportional to the electrical potential generated by the fibrillating heart;
(b) sampling said analog potential for a selected interval of time to obtain a set of time domain samples;
(c) detecting the power distribution of the fibrillating heart by machine transforming said time domain samples to a frequency domain power spectrum;
(d) detecting the median frequency which bisects the energy of said power spectrum; and
(e) measuring the approximate elapsed time since the onset of ventricular fibrillation by comparing said measured median frequency to a model median frequency of a composite model of median frequency as a function of tie, said model having been statistically derived from a plurality of prior measurements of median frequency and time elapsed since the onset of fibrillation for a plurality of similar subjects, wherein said composite model is a mathematical model algorithm statistically derived from said measurements of said similar subjects, wherein said model algorithm is at least two polynomials of at least first order and wherein said polynomials are substantially $FM(t) = 2.524762t + 5.057598$ for a measured median frequency slope greater than 0 and $FM(t) = -1.057669t + 17.043929$ for a median frequency slope less than or equal to 0.

9. A method for measuring a clinically useful characteristic of the fibrillating heart of a subject which correlates with the approximate elapsed time since the onset of ventricular fibrillation of the heart, and with the metabolic state of the heart after therapeutic intervention, the method comprising:
(a) connecting electrodes to the body of the subject and detecting from the electrodes an analog electrical potential which is proportional to the electrical potential generated by the fibrillating heart;
(b) sampling said analog potential for a selected interval of time to obtain a set of time domain samples;
(c) detecting the power distribution of the fibrillating heart by machine transforming said time domain samples to a frequency domain power spectrum;
(d) detecting the median frequency which bisects the energy of said power spectrum; and
(e) measuring the approximate elapsed time since the onset of ventricular fibrillation by comparing said measured median frequency to a model median frequency of a composite model of median frequency as a function of time, said model having been statistically derived from a plurality of prior measurements of median frequency and time elapsed since the onset of fibrillation for a plurality of similar subjects and wherein said composite model is a mathematical model algorithm having a at least polynomials of at least first order and is statistically derived from said measurements of said similar subjects, wherein, before the step for measuring the approximate elapsed time since the onset of ventricular fibrillation the median frequency is detected for at lest four selected time intervals and the slope of the median frequency as a function of time is machine computed and compared to the slope of said composite model to determine the time range of the model to utilize for detecting the approximate elapsed time since the onset of fibrillation.

* * * * *

UNITED STATES PATENT AND TRADEMARK OFFICE
CERTIFICATE OF CORRECTION

PATENT NO. : 5,077,667
DATED : Dec. 31, 1991
INVENTOR(S) : Charles G. Brown et al.

It is certified that error appears in the above-identified patent and that said Letters Patent is hereby corrected as shown below:

```
Claim 4, column 17, line 1, after "heart" insert --after--.
Claim 8, column 17, line 42, delete "s" and insert --is--;
claim 8, column 18, line 1, delete "tie" and insert --time--.
Claim 9, column 18, line 42, delete "a"; line 43, before
"polynomials" insert --two--.
```

Signed and Sealed this

Twentieth Day of April, 1993

Attest:

MICHAEL K. KIRK

*Attesting Officer*   *Acting Commissioner of Patents and Trademarks*